United States Patent
Shibata et al.

(10) Patent No.: US 11,385,095 B2
(45) Date of Patent: Jul. 12, 2022

(54) ULTRASONIC DISTANCE MEASURING DEVICE

(71) Applicant: DENSO CORPORATION, Kariya (JP)

(72) Inventors: Yuuya Shibata, Kariya (JP); Hironori Iwamiya, Kariya (JP); Akihiro Konno, Kariya (JP)

(73) Assignee: DENSO CORPORATION, Kariya (JP)

( * ) Notice: Subject to any disclaimer, the term of this patent is extended or adjusted under 35 U.S.C. 154(b) by 49 days.

(21) Appl. No.: 16/902,383

(22) Filed: Jun. 16, 2020

(65) Prior Publication Data
US 2021/0010846 A1 Jan. 14, 2021

(30) Foreign Application Priority Data
Jul. 10, 2019 (JP) .............................. JP2019-128734

(51) Int. Cl.
*G01F 23/2962* (2022.01)
*G01N 33/28* (2006.01)
*G01K 13/00* (2021.01)

(52) U.S. Cl.
CPC .......... *G01F 23/2962* (2013.01); *G01K 13/00* (2013.01); *G01N 33/28* (2013.01)

(58) Field of Classification Search
CPC ...... G01F 23/2962; G01F 13/00; G01N 33/28
USPC ............................................ 73/53.01, 290 V
See application file for complete search history.

(56) References Cited

U.S. PATENT DOCUMENTS

| | | | |
|---|---|---|---|
| 5,065,624 A * | 11/1991 | Fell | G01S 15/88 73/290 V |
| 5,319,973 A * | 6/1994 | Crayton | G01F 23/2962 181/124 |
| 5,793,705 A * | 8/1998 | Gazis | G10K 11/004 367/98 |
| 6,202,484 B1 * | 3/2001 | Willner | G01F 23/2962 73/290 V |
| 9,458,759 B2 * | 10/2016 | Rollinger | F16H 57/0412 |
| 2020/0033180 A1 | 1/2020 | Miyagawa et al. | |
| 2020/0033181 A1 | 1/2020 | Miyagawa et al. | |

FOREIGN PATENT DOCUMENTS

| | | |
|---|---|---|
| JP | 2006-145403 A | 6/2006 |
| JP | 2018-119808 A | 8/2018 |

* cited by examiner

*Primary Examiner* — Nimeshkumar D Patel
*Assistant Examiner* — Jean F Morello
(74) *Attorney, Agent, or Firm* — Posz Law Group, PLC

(57) ABSTRACT

An ultrasonic distance measuring device retrieves an ultrasonic wave propagation speed from a correlation between an output of a medium sensor and a corresponding ultrasonic wave propagation speed. The ultrasonic distance measuring device sets a propagation path detection period for detecting a detection signal, which corresponds to the ultrasonic wave reflected by a liquid surface, based on a longest propagation path length and a shortest propagation path length between the liquid surface and the retrieved propagation speed of the ultrasonic wave. The ultrasonic distance measuring device calculates a distance of the propagation path based on a time difference between a detection timing of the detection signal and an output timing of the ultrasonic wave in a propagation path detection period, and the propagation speed of the ultrasonic wave.

18 Claims, 10 Drawing Sheets

ULTRASONIC DISTANCE MEASURING DEVICE

CROSS REFERENCE TO RELATED APPLICATION

The present application claims the benefit of priority from Japanese Patent Application No. 2019-128734 filed on Jul. 10, 2019. The entire disclosures of the above application are incorporated herein by reference.

FIELD

The present disclosure relates to an ultrasonic distance measuring device that measures a distance of an ultrasonic wave propagation path between an ultrasonic element and a liquid surface of a liquid stored in a tank.

BACKGROUND OF THE DISCLOSURE

A conventional liquid level detecting device is configured to generate an ultrasonic wave toward a liquid of fuel and detect a position of a liquid level by detecting the ultrasonic wave reflected on the liquid surface.

The liquid level detecting device described above is configured to amplify and rectify a reception signal based on a detected ultrasonic wave and convert the signal into a detection signal. The liquid level detecting device is configured further to calculate a propagation time period of the ultrasonic wave, which is propagated to the liquid surface, reflected by the liquid surface, and returned from the liquid surface, based on the time when the detection signal becomes larger than a threshold level. The liquid level detecting device is configured to calculate the position of the liquid surface level based on the propagation time period and a speed of the ultrasonic wave calculated separately.

SUMMARY

According to the present disclosure, an ultrasonic distance measuring device is provided for measuring a distance of an ultrasonic wave propagation path to a liquid surface of a liquid stored in a tank. The ultrasonic distance measuring device is configured to perform generation of an ultrasonic wave by an ultrasonic element, conversion of an input ultrasonic wave into an electric signal, outputting a drive signal to the ultrasonic element for generation of the ultrasonic wave, outputting a detection signal when the electric signal of the ultrasonic element exceeds a threshold level, detecting a physical quantity depending on a propagation speed of the ultrasonic wave propagating a medium of a propagation path, and calculating a liquid surface level based on a time difference between output timing of the ultrasonic wave and a reception timing of the ultrasonic wave reflected by the liquid surface.

DETAILED DESCRIPTION OF THE EMBODIMENT

First Embodiment

Hereinafter, an ultrasonic distance measuring device 100 according to a first embodiment will be described below in detail with reference to FIG. 1 to FIG. 10. Three directions orthogonal to one another are referred to as an X direction, a Y direction, and a Z direction. The Z direction is the height direction.

Figure 1:
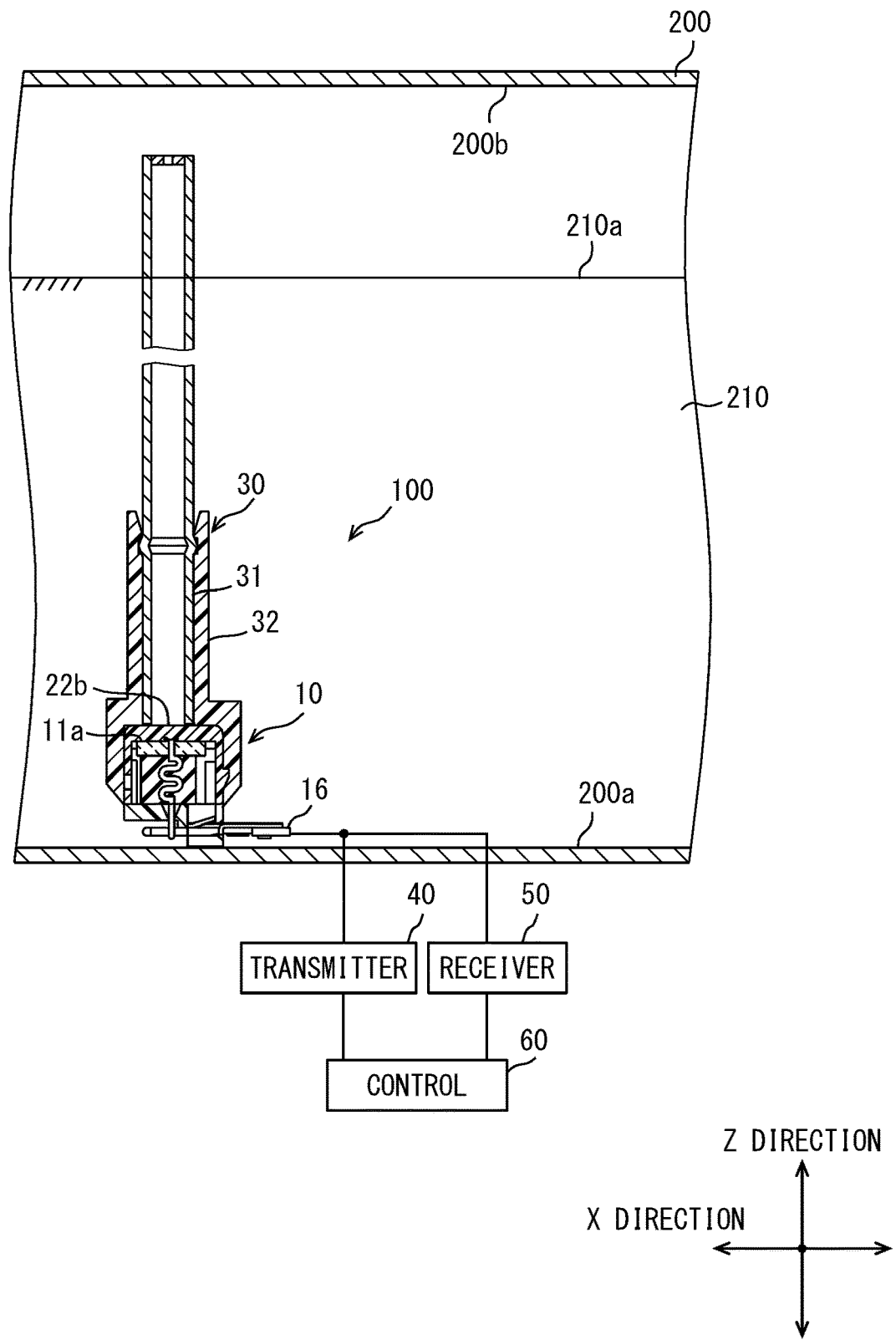
FIG. 1 is a schematic diagram showing an overall configuration of an ultrasonic distance measuring device.

The ultrasonic distance measuring device 100 is provided in a fuel tank 200 of a vehicle as shown in FIG. 1. The ultrasonic distance measuring device 100 has a function of detecting the position (liquid level) of a liquid surface 210a of fuel 210 stored in the fuel tank 200. The fuel 210 is, for example, gasoline. The fuel 210 is a liquid to be detected.

Figure 3:
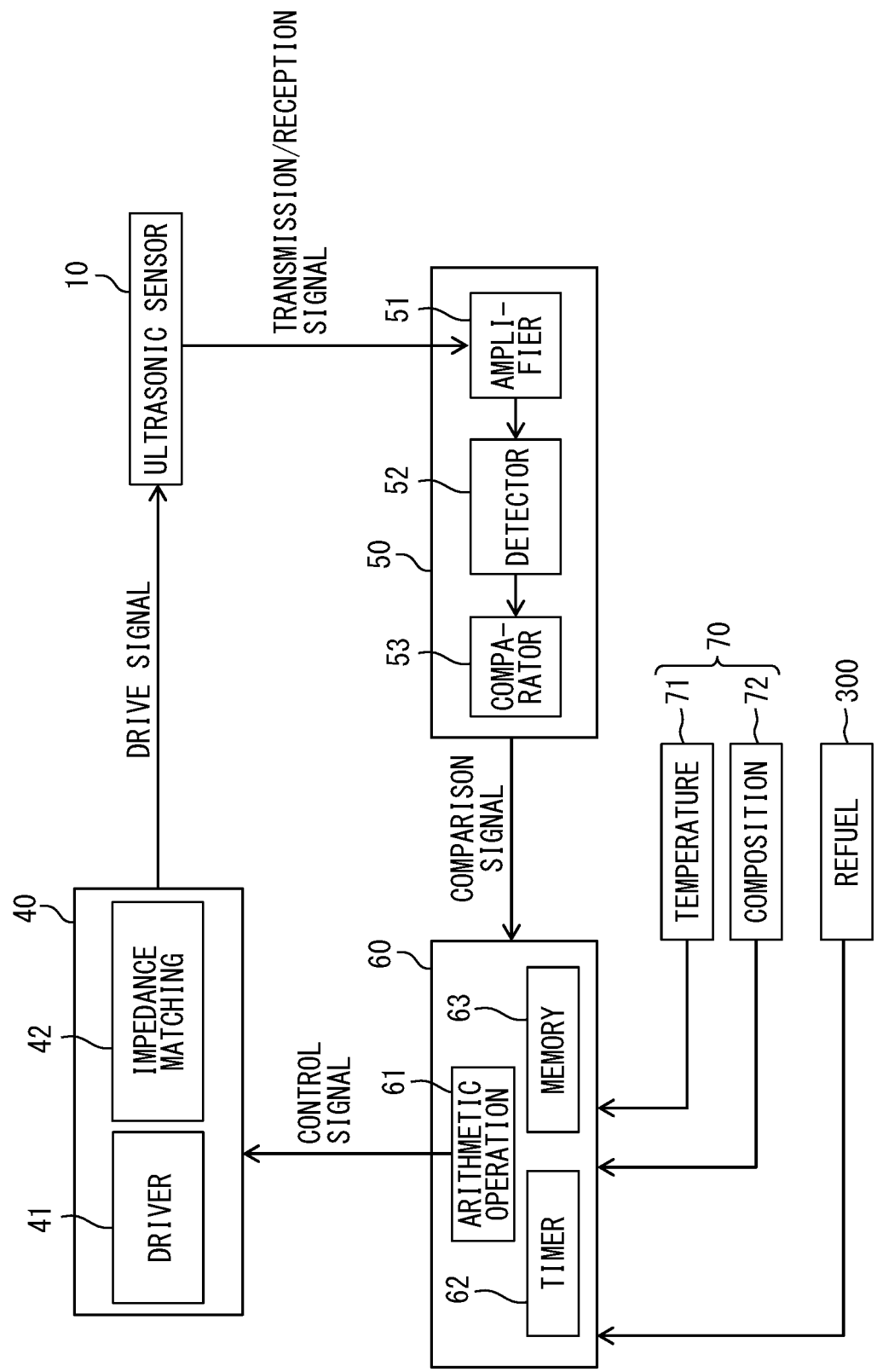
FIG. 3 is a block diagram showing electrical configuration of the ultrasonic distance measuring device.

As shown in FIG. 1 and FIG. 3, the ultrasonic distance measuring device 100 includes an ultrasonic sensor 10, a transmission pipe 30, a transmitter circuit 40, a receiver circuit 50, a control circuit 60, and a medium sensor 70. The ultrasonic sensor 10 is provided in the transmission pipe 30. The ultrasonic sensor 10 is electrically connected to each of the transmitter circuit 40 and the receiver circuit 50. Each of the transmission circuit 40 and the receiver circuit 50 is electrically connected to the control circuit 60. The medium sensor 70 is electrically connected to the control circuit 60.

The ultrasonic sensor 10 and the transmission pipe 30 are provided on a bottom surface 200a of the fuel tank 200. The ultrasonic sensor 10 and the transmission pipe 30 are in the fuel 210. An ultrasonic wave generated by the ultrasonic sensor 10 propagates through the fuel 210 in the fuel tank 200. The medium sensor 70 is also provided in the fuel 210.

The ultrasonic sensor 10 and the transmission pipe 30 may be provided on a top surface 200b of the fuel tank 200 separated from the bottom surface 200a in the Z direction. In case a vehicle is on a horizontal plane, the Z direction is along the vertical direction. The top surface 200b is located vertically above the liquid surface 210a of the fuel 210. In this case, the ultrasonic sensor 10 and the transmission pipe 30 are not in the fuel 210. The ultrasonic wave generated by the ultrasonic sensor 10 propagates through air existing above the liquid surface 210a in the fuel tank 200. In case that the ultrasonic sensor 10 is fixed to the bottom surface 200a or the top surface 200b, the ultrasonic distance measuring device 100 may not have the transmission pipe 30.

<Ultrasonic Sensor>

Figure 2:
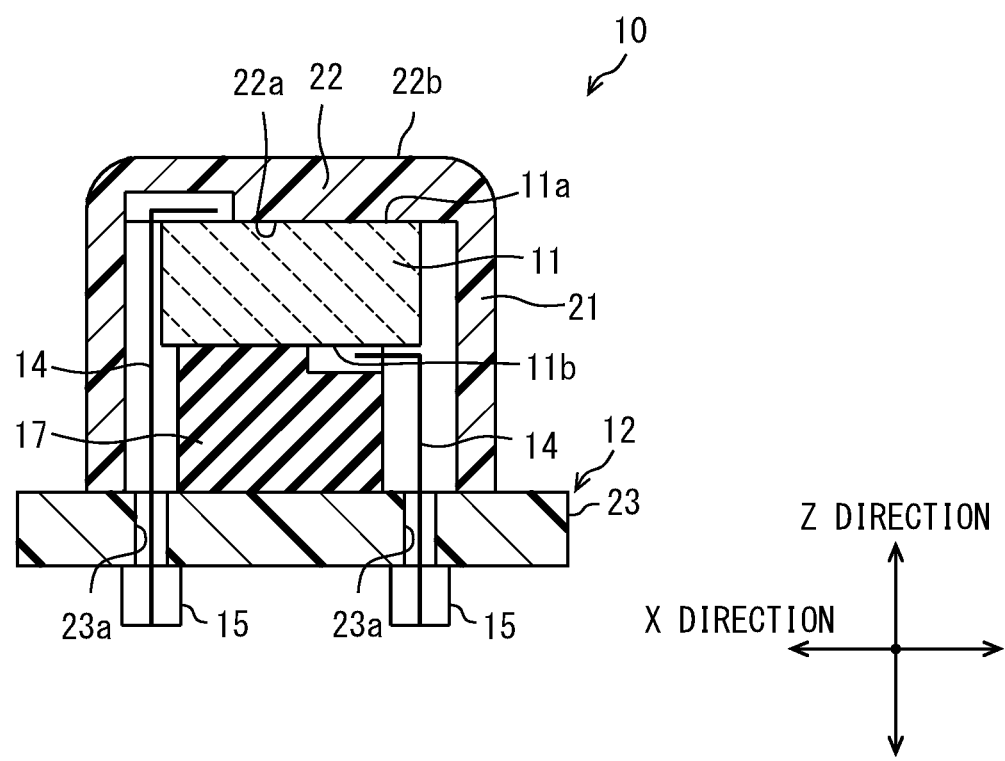
FIG. 2 is a cross-sectional view showing a configuration of an ultrasonic sensor.

The ultrasonic sensor 10 has an ultrasonic element 11 and a case 12 as shown in FIG. 2. The ultrasonic element 11 is an ultrasonic transducer that generates an ultrasonic wave. The ultrasonic element 11 is made of a piezoelectric material such as lead zirconate titanate (PZT) that generates a piezo effect. The piezoelectric material changes its volume when a voltage is applied, and generates a voltage when an external force is applied.

The ultrasonic element 11 has a disk shape whose thickness direction is in the Z direction. The ultrasonic element 11 has a contact surface 11a on its top and a back surface 11b on its bottom arranged in the Z direction. Electrodes are formed by printing on each of the contact surface 11a and the back surface 11b. The electrodes are formed over the entire surfaces of the contact surface 11a and the back surface 11b.

Ends of a pair of leads 14 are connected to the electrodes formed on the contact surface 11a and the back surface 11b by soldering or pressure welding. Other ends of the leads 14 are connected to electric terminals 15. The electric terminals 15 are connected to lead wires 16 shown in FIG. 1. The transmission circuit 40 and the reception circuit 50 are electrically connected to the lead wires 16.

The case 12 has an accommodation space for accommodating the ultrasonic element 11 therein. The case 12 is made of an insulating resin material. More specifically, the case 12 has a cylindrical portion 21, a bottom portion 22, and a lid portion 23. The bottom portion 22 is integrally formed with connected to the cylindrical portion 21. The lid portion 23 is a separate member from the cylindrical portion 21 and the bottom portion 22.

The cylindrical portion 21 extends in its axial direction which is the Z direction. One of the axial ends of the cylindrical portion 21 is closed by the bottom portion 22. The other of the axial ends of the cylindrical portion 21 is open. The lid portion 23 is coupled to the cylindrical portion 21 in a manner to to close the other axial end of the cylindrical portion 21. Thereby, an inside space of the cylindrical portion 21 is a closed space. The inside space of the cylindrical portion 21 is the accommodation space of the case 12. The lid portion 23 has through holes 23a for passing end portions of the leads 14 out of the accommodation space.

In this accommodation space, a vibration isolator 17 is provided in addition to the ultrasonic element 11. The vibration isolator 17 is formed of a flexible resin material or rubber material. As a material for this formation, for example, nitrile rubber is used.

In the accommodation space, the ultrasonic element 11 is located on the bottom portion 22 side, which is opposite to the lid portion 23. The vibration isolator 17 is located on the lid portion 23 side. In case the lid portion 23 is fixed to the cylindrical portion 21, the vibration isolator 17 is compressed between the ultrasonic element 11 and the lid portion 23. The vibration isolator 17 is elastically deformed in the Z direction. The vibration isolator 17 generates a restoring force in a direction away from itself in the Z direction. Due to this restoring force, the contact surface 11a of the ultrasonic element 11 keeps contacting an inner surface 22a of the bottom portion 22. At the same time, the vibration isolator 17 also keeps contacting the lid portion 23.

In the above configuration, the ultrasonic element 11 vibrates in the Z direction in which the contact surface 11a and the back surface 11b are arranged, when a drive signal for generating an ultrasonic wave is applied to the ultrasonic element 11 from the transmitter circuit 40. Due to this vibration, the bottom portion 22 of the case 12 in contact with the ultrasonic element 11 also vibrates in the Z direction. The fuel 210 in contact with an outer surface 22b of the bottom portion 22 also vibrates. The Ultrasonic wave is generated in the fuel 210.

Conversely, the ultrasonic element 11 is compressed between the bottom portion 22 and the vibration isolator 17 in the Z direction, when the bottom portion 22 vibrates due to vibration applied from the outside. Thereby, a voltage is generated in the ultrasonic element 11. This voltage generated in correspondence to the received vibration is input to the receiver circuit 50 as an ultrasonic reception signal.

It should be noted that reverberation vibration remains in the ultrasonic element 11 after generating the ultrasonic wave. The vibration isolator 17 has a function of suppressing the occurrence of the reverberation vibration. The vibration isolator 17 further prevents the ultrasonic wave generated by the ultrasonic element 11 from leaking out of the accommodation space of the case 12 through the lid portion 23.

<Transmission Pipe>

The transmission pipe 30 propagates the ultrasonic wave generated from the ultrasonic sensor 10 toward the liquid surface 210a of the fuel 210, and propagates the ultrasonic wave reflected on the liquid surface 210a to the ultrasonic element 11 again (propagation path).

The transmission pipe 30 has a vertical pipe 31 that forms the propagation path, and a housing 32 that connects the vertical pipe 31 and the case 12 of the ultrasonic sensor 10.

The vertical pipe 31 is formed of, for example, a metal material such as an alloy for aluminum die casting, or an insulating resin material. The vertical pipe 31 extends in the Z direction. One of two openings of the vertical pipe 31 is closed by the bottom portion 22 of the case 12 on the bottom surface 200a side. The other of the two openings of the vertical pipe 31 is open on the top surface 200b side.

The length of the vertical pipe 31 in the Z direction is set such that its other end protrudes more toward the top surface 200b side than the liquid surface 210a under a condition that the fuel tank 200 is fully filled with the fuel 210. Although not shown, the vertical pipe 31 is formed with communication holes for communicating its inside space with its outside space. Thereby, the fuel 210 enters the inside space of the vertical pipe 31 through the communication holes. The communication holes are provided such that the liquid surface 210a of the fuel 210 inside the vertical pipe 31 and the liquid surface 210a of the fuel 210 outside the vertical pipe 31 are equal.

With the configuration described above, when the ultrasonic wave is generated by the ultrasonic element 11, the ultrasonic wave propagates from the opening on one axial end side of the vertical pipe 31 to the opening on the other axial end side. A part of the ultrasonic wave is incident on the liquid surface 210a and is reflected. A part of a reflected ultrasonic wave (liquid surface wave) is incident on the outer surface 22b of the ultrasonic sensor 10. Thereby, the ultrasonic element 11 vibrates. A reception signal is generated by the ultrasonic element 11 based on the liquid surface wave.

Assuming that a propagation speed of the ultrasonic wave is vp and a propagation time period from a timing when the ultrasonic wave is output to a timing when the liquid surface wave returns to the ultrasonic element 11 is tp, a propagation path length Lp is determined mathematically as follows.

$$Lp = vp \times tp/2.$$

A housing 32 is formed of a resin material having excellent stability with respect to the fuel 210. The housing 32 covers outer surfaces of one axial end opening side of the vertical pipe portion 31 and the cylindrical portion 21. The ultrasonic sensor 10 is fixed to the vertical pipe 31 by the housing 32.

<Transmitter Circuit>

As shown in FIG. 3, the transmitter circuit 40 includes a driver circuit 41 and an impedance matching circuit 42. The driver circuit 41 has a switching element provided between a power supply and the ground. The impedance matching circuit 42 has a diode provided between the power supply and the switching element. A cathode electrode of the diode is connected to the power supply. The impedance matching circuit 42 has a primary pulse transformer connected in parallel to the diode, and a secondary pulse transformer magnetically coupled to the primary pulse transformer. The lead wires 16 are connected to both ends of the secondary pulse transformer for connection to the ultrasonic sensor 10.

The switching element is controlled to open (OFF) and close (ON) by a control signal input from the control circuit 60. When the switching element changes from the open state to the closed state, a current flows as the drive signal through the pulse transformer. Thereby, a voltage is applied to the ultrasonic element 11 via the lead wires 16.

<Receiver Circuit>

The receiver circuit 50 has an amplifier circuit 51, a detector circuit 52, and a comparator circuit 53. The amplifier circuit 51 is connected to the lead wires 16 connected to both ends of the secondary pulse transformer. Therefore, the drive signal (transmission signal) input from the transmitter circuit 40 to the ultrasonic element 11 and the reception signal input from the ultrasonic element 11 are input to the amplifier circuit 51.

The amplifier circuit 51 amplifies each of the transmission signal and the reception signal. The amplifier circuit 51 outputs a signal (amplified signal) produced by amplifying each of the transmission signal and the reception signal to the detector circuit 52.

The detector circuit 52 performs half-wave rectification on the amplified signal, and generates a detection signal that connects peaks of a plurality of half-wave rectified signals. The detector circuit 52 outputs the detection signal to the comparator circuit 53.

The comparator circuit 53 compares the detection signal with a threshold level. The comparator circuit 53 generates a comparison signal having a high level and a low level when the detection signal is larger and smaller than the threshold level, respectively. The comparator circuit 53 outputs the comparison signal to the control circuit 60. The comparator circuit 53 may generate a comparison signal having a low level and a high level when the detection signal is larger and smaller than the threshold level, respectively. The comparison signal corresponds to the detection signal.

<Control Circuit>

The control circuit 60 has an arithmetic operation circuit 61, a timer 62 and a memory 63. The arithmetic operation circuit 61 periodically performs elapsed time detection processing, propagation speed detection processing and propagation path detection processing described later, for example, every 100 milliseconds (ms). Alternatively, the arithmetic operation circuit 61 performs the elapsed time detection processing, the propagation speed detection processing and the propagation path detection processing as event processing, when an ignition switch of a vehicle is switched from OFF to ON. The arithmetic operation circuit 61 is programmed to execute various processing described below and operates as a retrieval circuit, a period circuit, and a calculation circuit. The memory 63 is a storage unit.

Figure 4:
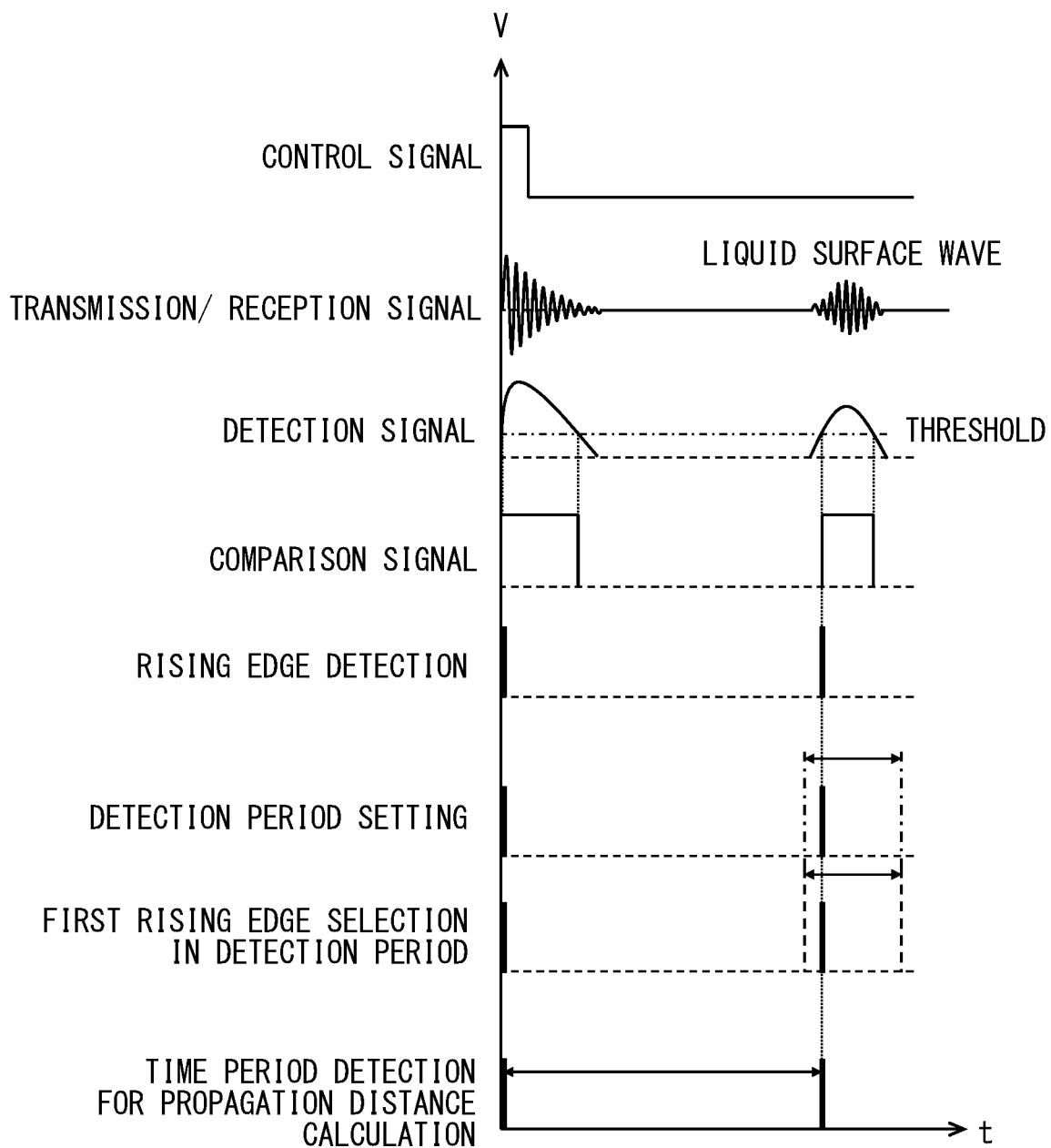
FIG. 4 is a timing chart showing signal processing.

The arithmetic operation circuit 61 outputs the control signal shown in FIG. 4 to the transmitter circuit 40. When receiving the control signal, the transmitter circuit 40 outputs the drive signal to the ultrasonic element 11. When the drive signal is input, the ultrasonic sensor 10 outputs the ultrasonic wave to the fuel 210 in the transmission pipe 30. Part of the ultrasonic wave is reflected by the liquid surface 210a and returns to the ultrasonic sensor 10 as the liquid surface wave.

Upon receiving the ultrasonic wave, the ultrasonic sensor 10 converts the ultrasonic wave into a voltage and generates an electric signal as the reception signal. The ultrasonic sensor 10 outputs the reception signal to the receiver circuit 50.

When the reception signal is input, the receiver circuit 50 amplifies the reception signal and converts it into the detection signal. The receiver circuit 50 compares the detection signal with the threshold value to generate the comparison signal. The receiver circuit 50 outputs the comparison signal to the arithmetic operation circuit 61 of the control circuit.

As described above, the drive signal is input not only to the ultrasonic sensor 10 but also to the receiver circuit 50. Therefore, the receiver circuit 50 converts the drive signal into the detection signal and generates the comparison signal before converting the reception signal into the detection signal and generating the comparison signal. The receiver circuit 50 also outputs the comparison signal based on the drive signal to the arithmetic operation circuit 61.

The arithmetic operation circuit 61 detects a timing (rising edge) at which the voltage level of each of the plurality of inputted comparison signals rises from the low level to the high level. The arithmetic operation circuit 61 recognizes the rising edge detected first as a timing (output timing) of outputting the ultrasonic wave from the ultrasonic sensor 10, by receiving the drive signal to the ultrasonic sensor 10.

The arithmetic operation circuit 61 calculates a time period which is a time difference between the rising edge and a rising edge detected thereafter based on the time measured by the timer 62. Thus, the arithmetic operation circuit 61 calculates a period of elapsed time until the ultrasonic wave output from the ultrasonic sensor 10 returns to the ultrasonic sensor 10. At the same time, the arithmetic operation circuit 61 stores the elapsed time period in the memory 63.

<Number of Rising Edges>

As shown in FIG. 4, for example, the ultrasonic wave received by the ultrasonic sensor 10 after outputting the ultrasonic wave is assumed to be one of the liquid surface waves reflected by the liquid surface 210a. Therefore, the number of rising edges detected by the arithmetic operation circuit 61 is assumed to be one, excluding the rising edge corresponding to the drive signal.

Figure 5:
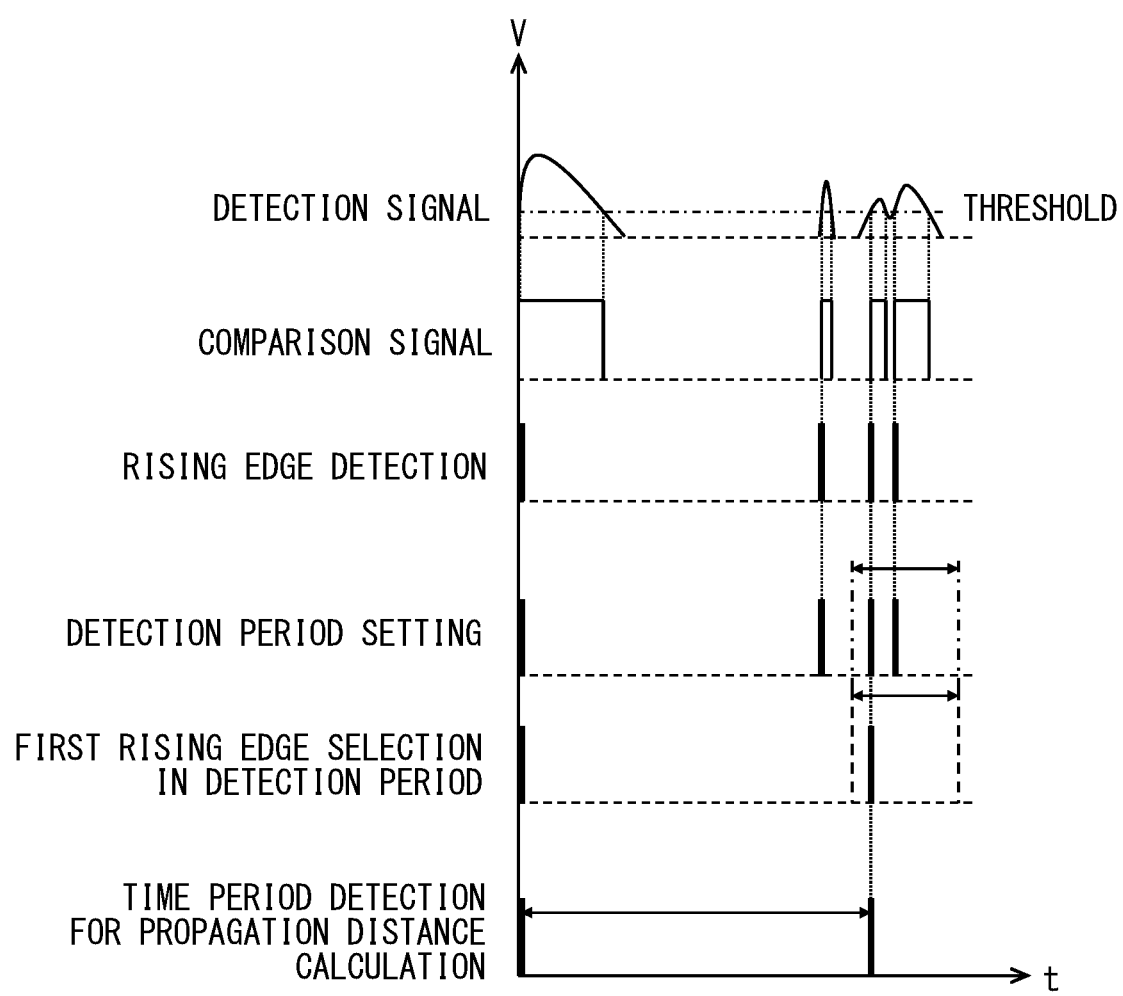
FIG. 5 is a timing chart showing signal processing when noise is mixed.

However, for example, noise may overlap the detected signal as shown in FIG. 5. In this case, more than two rising edges are detected. In the example of FIG. 5, three rising edges are detected. This makes it impossible to determine which rising edge is based on the liquid surface wave.

To solve such a problem, the arithmetic operation circuit 61 sets a propagation path detection period for detecting the rising edge, which actually corresponds to the liquid surface wave.

It should be noted that the position of the liquid surface 210a changes depending on the amount of the fuel 210 stored in the fuel tank 200. Therefore, even in case that the ultrasonic wave propagation speed vp is constant, the timing at which the liquid surface wave is detected differs depending on the position of the liquid level 210a. Further, the propagation speed vp of the ultrasonic wave changes depending on a temperature. Therefore, the timing at which the liquid surface wave is detected differs depending on the temperature of the fuel 210.

The arithmetic operation circuit 61 sets, as described later, the propagation path detection period by which the detection timing of the liquid surface wave is detected without being affected by the noise even in case that the position of the liquid surface 210a and the propagation speed vp change.

<Medium Sensor>

The medium sensor 70 has a function of detecting a physical quantity that depends on the speed of the ultrasonic wave propagating through the medium of the propagation path. The medium sensor 70 has a function of detecting a temperature and composition of the medium of the propagation path as the physical quantities. Specifically, the medium sensor 70 has a temperature sensor 71 and a composition sensor 72.

The temperature sensor 71 and the composition sensor 72 are located in the fuel 210. The Temperature sensor 71 detects the temperature of the fuel 210. The composition sensor 72 detects the composition of the fuel 210. These detection results are input to the arithmetic operation circuit 61 described above.

The temperature and the composition of the fuel 210 are detected, because the ultrasonic wave propagation speed vp differs depending on the temperature and the composition of the fuel 210 through which the ultrasonic wave propagates. The fuel 210 of the present embodiment has such a property that the propagation speed vp increases as the temperature decreases. The memory 63 stores a correlation between the temperature at which the ultrasonic wave propagates and the ultrasonic wave propagation speed vp.

The arithmetic operation circuit 61 retrieves the ultrasonic wave propagation speed vp from a correlation stored in the memory 63 based on the temperature and the composition of the fuel 210 input from the temperature sensor 71 and the composition sensor 72. The arithmetic operation circuit 61 sets the following propagation path detection period based on the retrieved propagation speed vp.

<Propagation Path Detection Period>

The propagation time period tp from when the ultrasonic wave is output from the ultrasonic sensor 10 to when the liquid surface wave reflected by the liquid surface 210a returns to the ultrasonic sensor 10 depends on a propagation path length Lp and the propagation speed vp of the ultrasonic wave.

The propagation time period tp becomes the shortest under the constant propagation speed vp when the propagation path length Lp is the shortest. The propagation time period tp becomes the longest when the propagation path length Lp is the longest. The timing at which the rising edge corresponding to the liquid surface wave is detected is assumed to be between the time period when the propagation time period tp is the shortest and the time period when the propagation time period tp is the longest. If a rising edge is detected in a period other than the period set between the shortest propagation time period tp and the longest propagation time period tp, such a rising edge is assumed to be not a signal corresponding to the liquid surface wave.

The time period when the propagation path length Lp is the shortest is when the fuel tank 200 has almost no fuel 210. The longest propagation path length Lp is when the fuel tank 200 is full of fuel 210. In the following description, for the sake of simplicity, the propagation path length when there is almost no fuel 210 is referred to as a shortest propagation path length Ll, and the propagation path length when the fuel 210 is full is referred to as a longest propagation path length Lh. The shortest propagation path length Ll and the longest propagation path length Lh are stored in the memory 63.

The shortest propagation path length Ll stored in the memory 63 may be slightly shorter than a propagation path length when there is almost no fuel 210 in the fuel tank 200. Similarly, the longest propagation path length Lh stored in the memory 63 may be slightly longer than a propagation path length when the fuel tank 200 is full of fuel 210.

Figure 6:
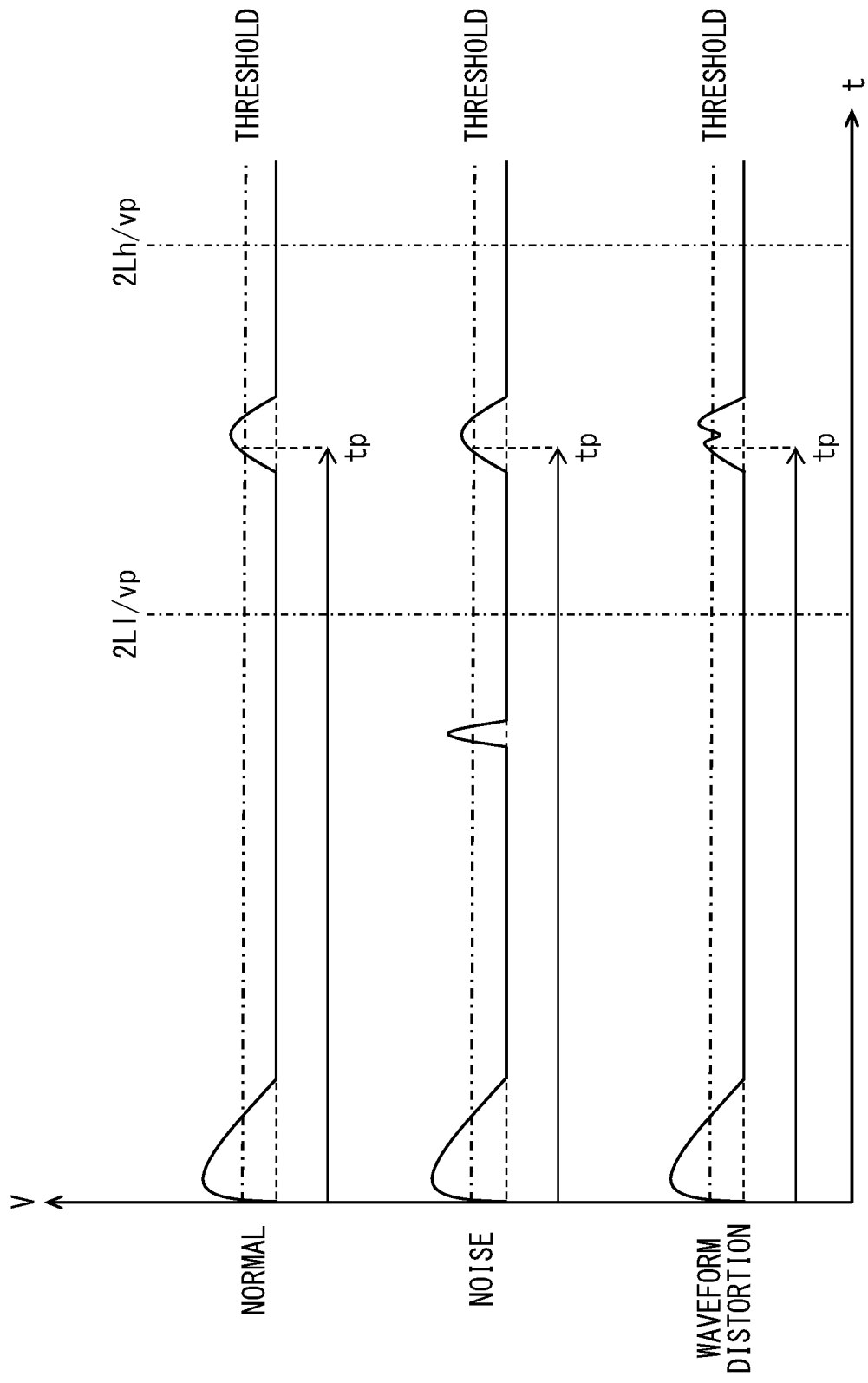
FIG. 6 is a timing chart showing setting of a detection period.

In case of setting the propagation path detection period for the first time, as shown in FIG. 6, for example, a lower limit value and an upper limit value of the detection period are defined. The lower limit value of the propagation path detection period is represented as 2Ll/vp mathematically. The upper limit value of the propagation path detection period is expressed as 2Lh/vp.

The arithmetic operation circuit 61 detects the rising edge of the comparison signal input during the propagation path detection period defined as above. The arithmetic operation circuit 61 calculates the time difference between the rising edge detected within the propagation path detection period and the rising edge detected first in a period before the propagation path detection period as the propagation time period tp. The arithmetic operation circuit 61 stores the calculated propagation time period tp in the memory 63.

In some cases, a plurality of rising edges may be detected in the propagation path detection period as shown in FIG. 5 due to noise or the like. In this case, the arithmetic operation circuit 61 selects the rising edge detected in the shortest time period in the propagation path detection period as the rising edge corresponding to the liquid surface wave. The timing at which the rising edge corresponding to the liquid surface wave rises is a liquid level timing.

The arithmetic operation circuit 61 calculates the propagation path length Lp based on the calculated propagation time period tp and the propagation speed vp. The propagation path length Lp is expressed as Lp=vp×tp/2 mathematically. The arithmetic operation circuit 61 stores the calculated propagation path length Lp in the memory 63.

In case of setting the propagation path detection period again, the memory 63 already stores the propagation time period tp calculated during the previous setting processing of the propagation path detection period. The correlation between the propagation speed and a waveform length Lw of the liquid surface wave is stored in the memory 63 in advance.

The arithmetic operation circuit 61 retrieves the waveform length Lw of the liquid surface wave, which corresponds to the propagation speed vp from the correlation stored in the memory 63. Then, the arithmetic operation circuit 61 updates the propagation path detection period based on the retrieved waveform length Lw of the liquid surface wave and the propagation time period tp stored in the memory 63. According to this updating, the propagation path detection period is appropriately narrowed as exemplarily shown in FIG. 7.

This "waveform length" does not necessarily indicate the wavelength determined by dividing the propagation speed of the ultrasonic wave by the frequency. For example, it shows the length of the waveform of the detection signal shown in FIG. 4. It shows the length of a range which is larger than a reference value such as 0 V and lower than a threshold value is shown.

The updated lower limit value of the propagation path detection period is expressed as tp-Lw/2. The upper limit is expressed as tp+Lw/2. A center value of the updated propagation path detection period is set to the propagation time period tp stored in the memory 63. The width of the propagation path detection period is the length Lw of the waveform of the liquid surface wave.

Figure 7:
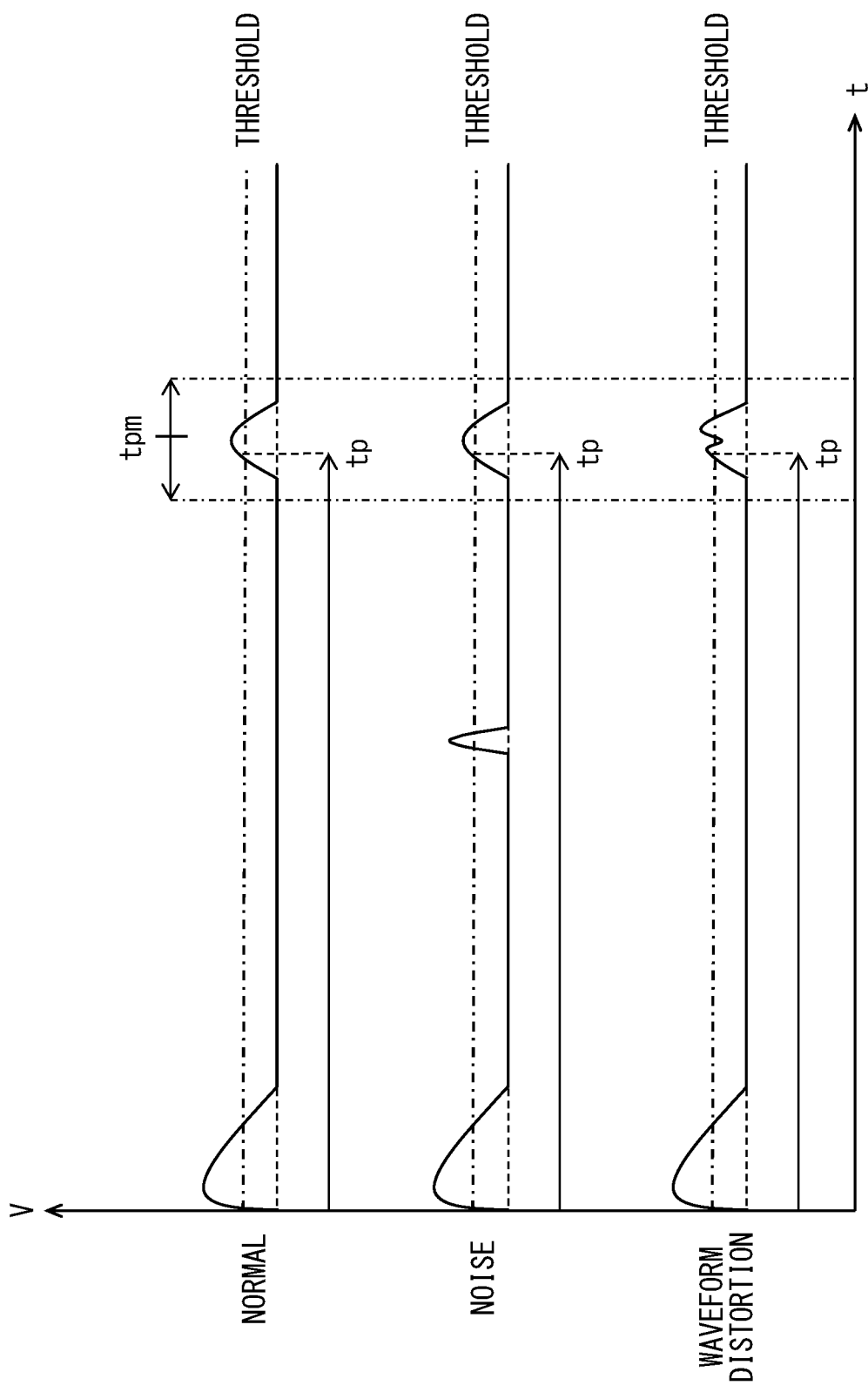
FIG. 7 is a timing chart showing updating of the detection period.

It should be noted that the detection signal corresponding to the liquid surface wave exceeds the threshold level because the detection signal takes time to take a peak value. Therefore, the center value of the propagation path detection period may be set slightly later than the propagation time period tp stored in the memory 63. The width of the propagation path detection period may be set to a value determined by multiplying the length Lw of the liquid surface wave by a coefficient which is equal to or larger than 1. Further, the length Lw of the waveform of the liquid surface wave may be stored in the memory 63 as a fixed value. In FIG. 7, the propagation time period stored in the memory 63 is shown as tpm.

Next, the elapsed time detection processing, the propagation speed detection processing and the propagation path detection processing executed by the arithmetic operation circuit 61, specifically a programmed digital computer, will be described with reference to FIG. 8 to FIG. 10.

<Elapsed Time Detection Processing>

Figure 8:
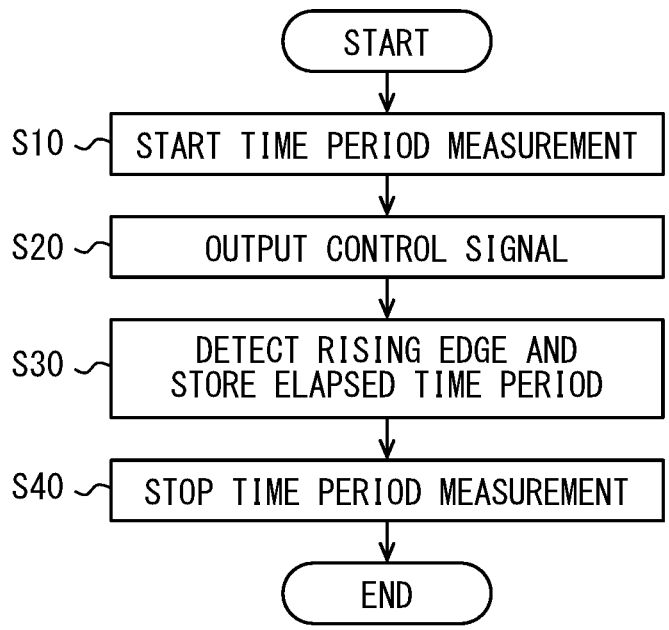
FIG. 8 is a flowchart showing elapsed time detection processing.

FIG. 8 shows the elapsed time detection processing in a simplified manner. When a periodic or a predetermined event task starts up, the arithmetic operation circuit 61 starts executing step S10 shown in FIG. 8. In step S10, the arithmetic operation circuit 61 starts measuring time by the timer 62.

In step S20, the arithmetic operation circuit 61 outputs the control signal to the transmitter circuit 40. As a result, the drive signal and the reception signal are input to the receiver circuit 50. The arithmetic operation circuit 61 receives the comparison signal based on these two types of signals.

In step S30, the arithmetic operation circuit 61 detects a rising edge of the comparison signal input from the receiver circuit 50. The arithmetic operation circuit 61 calculates the time difference between the rising edge detected first and the rising edge detected thereafter as the elapsed time period, which is until the ultrasonic wave output from the ultrasonic sensor 10 returns to the ultrasonic sensor 10. The arithmetic operation circuit 61 stores the elapsed time in the memory 63.

In step S40, the arithmetic operation circuit 61 stops the time measurement executed by the timer 62. The timing of the end of the time measurement is set to be later than a time, at which time the liquid surface wave returns to the ultrasonic sensor 10, under a condition that the propagation speed vp of the ultrasonic wave is the slowest under a use environment temperature of the ultrasonic element 11 and the fuel tank 200 is filled fully with the fuel 210. The above is the elapsed time detection processing.

<Propagation Speed Detection Processing>

Figure 9:
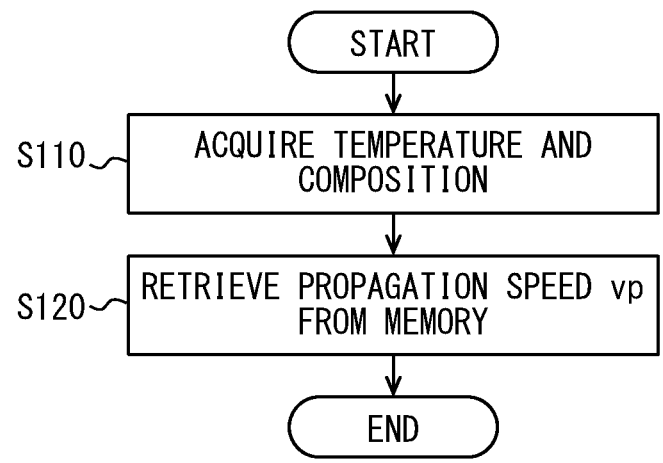
FIG. 9 is a flowchart showing propagation speed detection processing.

FIG. 9 schematically shows propagation speed detection processing. After completing the execution of the elapsed time detection processing, the arithmetic operation circuit 61 starts executing step S110 shown in FIG. 9.

In step S110, the arithmetic operation circuit 61 acquires outputs of the temperature sensor 71 and the composition sensor 72. Thereafter, the arithmetic operation circuit 61 executes step S120.

In step S120, the arithmetic operation circuit 61 retrieves the ultrasonic wave propagation speed vp from the correlation stored in the memory 63 based on the outputs of the temperature sensor 71 and the composition sensor 72. The above is the propagation speed detection processing.

<Propagation Path Detection Processing>

Figure 10:
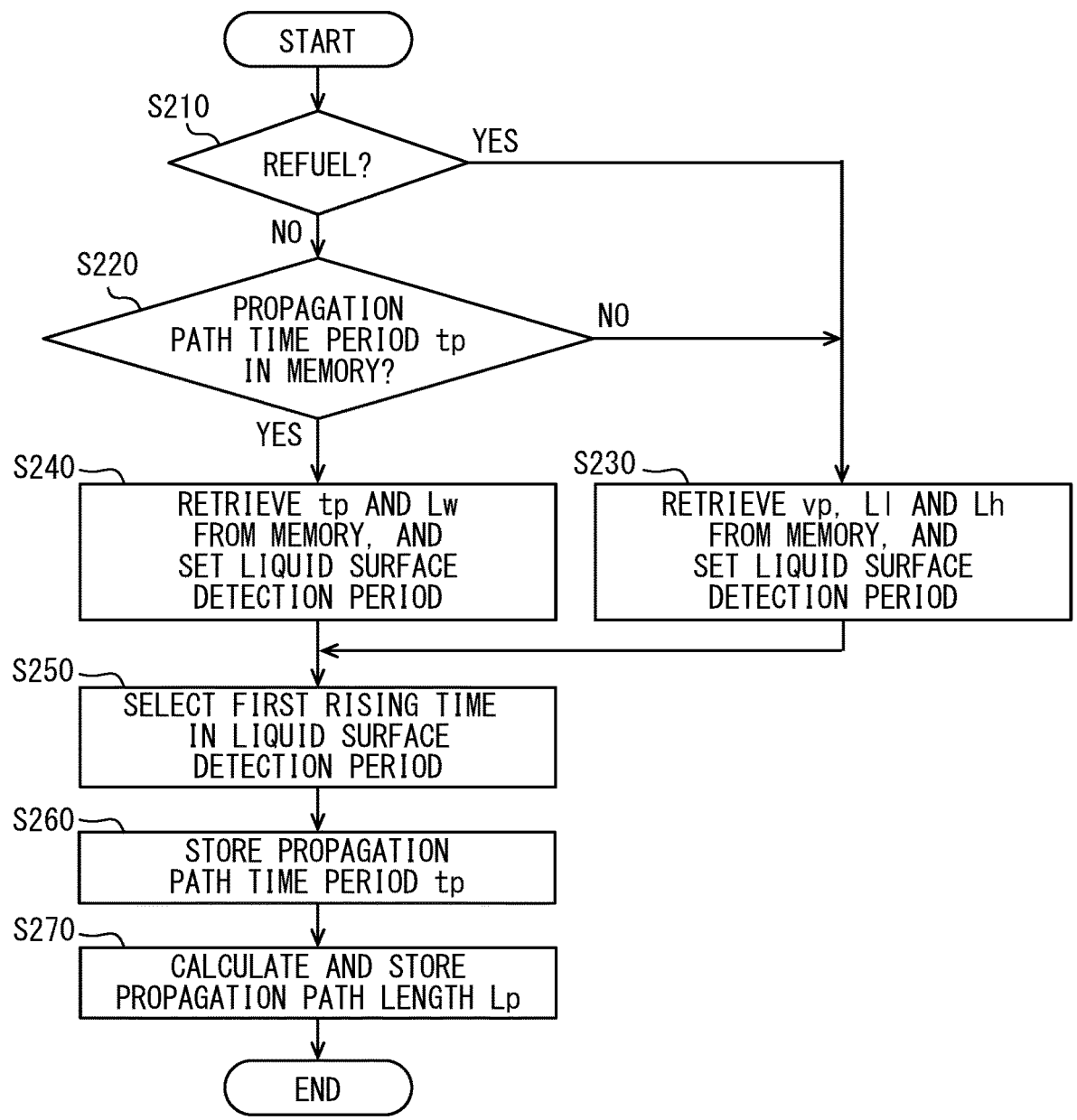
FIG. 10 is a flowchart showing propagation path detection processing.

FIG. 10 shows an example of propagation path detection processing in a simplified manner. As shown in FIG. 3, the vehicle is provided with a refueling sensor 300 for determining whether refueling has occurred. After completing the execution of the propagation speed detection processing, the arithmetic operation circuit 61 starts executing step S210 shown in FIG. 10.

In step S210, the arithmetic operation circuit 61 acquires the output of the refueling sensor 300. Based on this output, the arithmetic operation circuit 61 checks whether the fuel tank 200 has been refueled with the fuel 210. If there is no refueling, the arithmetic operation circuit 61 executes step S220. If refueling has been made, the arithmetic operation circuit 61 executes step S230.

In step S220, the arithmetic operation circuit 61 checks whether the propagation time period tp is stored in the memory 63. In case the propagation time period tp is stored in the memory 63, the arithmetic operation circuit 61 executes step S240. In case the propagation time period tp is not stored in the memory 63, the arithmetic operation circuit 61 executes step S230.

In step S240, the arithmetic operation circuit 61 retrieves the propagation time period tp and the propagation path length Lw of the liquid surface wave stored in the memory 63. Then, the arithmetic operation circuit 61 calculates the lower limit value tp−Lw/2 and the upper limit value tp+Lw/2 of the propagation path detection period. The arithmetic operation circuit 61 then executes step S250.

In step S230, the arithmetic operation circuit 61 retrieves the shortest propagation path length Ll and the longest propagation path length Lh from the memory 63. Then, the arithmetic operation circuit 61 calculates the lower limit value 2Ll/vp and the upper limit value 2Lh/vp of the propagation path detection period based on these retrieved propagation path lengths and the propagation speed vp retrieved from the memory 63 in step S120 of the propagation speed detection processing. Thereafter, the arithmetic operation circuit 61 executes step S250.

In case the arithmetic operation circuit 61 executes the propagation path detection processing for the first time, the propagation time period tp is not stored in the memory 63. Therefore, when the propagation path detection processing is executed for the first time, the arithmetic operation circuit 61 executes step S230 instead of step S240. The arithmetic operation circuit 61 executes step S240 in the propagation path detection processing executed subsequently. As a result, the propagation path detection period is updated. The width of the propagation path detection period is reduced.

In step S250, the arithmetic operation circuit 61 selects the rising edge of the comparison signal input during the propagation path detection period. In case there are plural rising edges in the propagation path detection period, the arithmetic operation circuit 61 selects the rising edge which is closest to the lower limit value of the propagation path detection period. Then, the arithmetic operation circuit 61 executes step S260.

In step S260, the arithmetic operation circuit 61 stores the elapsed time corresponding to the rising edge selected in step S250 in the memory 63 as the propagation time period tp. This elapsed time period has already been calculated in step S30 in the elapsed time detection processing. Thereafter, the arithmetic operation circuit 61 executes step S270.

In step S270, the arithmetic operation circuit 61 retrieves the elapsed time period (propagation time period tp) and the propagation speed vp selected in step S250 from the memory 63. Then, the arithmetic operation circuit 61 calculates the propagation path length Lp=vp×t02/2. The arithmetic operation circuit 61 stores the calculated propagation path length Lp in the memory 63. The above is the propagation path detection processing.

By detecting the propagation path length Lp in the above-described processing, the arithmetic operation circuit 61 calculates a height position (liquid level) of the liquid surface 210a in the Z direction based on the propagation path length Lp and the length of the ultrasonic sensor 10 in the Z direction. Then, the arithmetic operation circuit 61 outputs data including the calculated liquid level to, for example, a liquid level display device of the vehicle.

<Operational Effects>

Next, the operation and effect of the ultrasonic distance measuring device 100 will be described.

It is assumed that the ultrasonic wave reflected by the liquid surface 210a returns to the ultrasonic element 11 between the time when the ultrasonic wave propagation time is the longest and the time when the ultrasonic wave propagation time is the shortest. If the rising edge is detected in a period other than the detection period set between the shortest propagation time period tp and the longest propagation time period tp, such a rising edge is assumed to be not a signal which corresponds to the liquid surface wave.

Therefore, the ultrasonic distance measuring device 100 according to the present embodiment sets the propagation path detection period, which is for detecting the rising edge corresponding to the liquid surface wave, based on the shortest propagation path length Ll and the longest propagation path length Lh of the ultrasonic wave propagation path and the ultrasonic wave propagation speed vp. The ultrasonic distance measuring device 100 calculates the propagation path length Lp based on the elapsed time (propagation time period tp) from the output of the ultrasonic wave of the rising edge during the propagation path detection period and the propagation speed vp of the ultrasonic wave.

Accordingly, measurement of the propagation path length Lp by a signal that is not based on the position of the liquid surface 210a is suppressed. A decrease in distance measurement accuracy is suppressed.

In case the propagation time period tp is stored in the memory 63, the arithmetic operation circuit 61 updates the propagation path detection period based on the propagation time period tp and the length Lw of the liquid surface wave. This narrows the width of the propagation path detection period. Accordingly, measurement of the propagation path length Lp by the signal that is not based on the position of the liquid surface 210a is suppressed.

The memory 63 stores the correlation between the propagation speed (fuel temperature) and the length of the liquid surface wave waveform. The arithmetic operation circuit 61 retrieves the waveform length Lw of the liquid surface wave, which corresponds to the propagation speed vp from the correlation stored in the memory 63. According to this, the width of the propagation path detection period is narrowed more appropriately than in a configuration in which the length of the waveform is stored as a fixed value in the memory 63.

Although the present disclosure is described with reference to the preferred embodiment, the present disclosure is not limited to the above-described embodiment but may be implemented with various modifications without departing from the spirit of the present disclosure.

First Modification

In the present embodiment, for example, as shown in FIG. 10, when the propagation time period tp is stored in the memory 63, the liquid level detection period is updated using the stored propagation time period tp. However, the liquid level detection period may be set based on the propagation speed vp, the shortest propagation path length Ll and the longest propagation path length Lh without executing steps S220 and S240.

Second Modification

Figure 11:
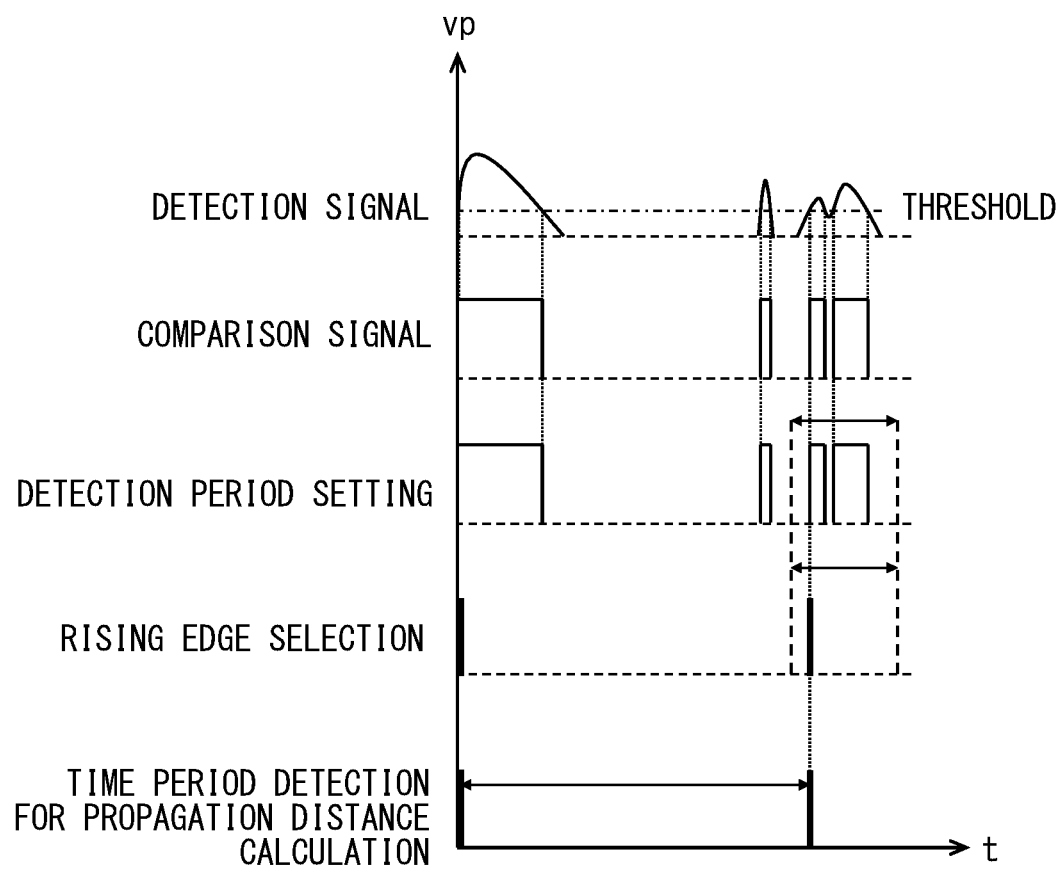
FIG. 11 is a block diagram showing a modified example of signal processing.

In the present embodiment, the arithmetic operation circuit 61 is exemplified to set the propagation path detection period after calculating the elapsed time period. However, the arithmetic operation circuit 61 may calculate the elapsed time period after setting the propagation path detection period, for example, as shown in FIG. 11.

Other Modifications

In the present embodiment, the ultrasonic distance measuring device 100 has been described as detecting the position of the liquid surface 210a of the fuel 210 in the fuel tank 200. However, the liquid to be detected by the ultrasonic distance measuring device 100 is not limited to the fuel 210 such as gasoline. The liquid to be detected may be, for example, washer liquid, coolant liquid, brake oil, automatic transmission fluid.

In the present embodiment, the arithmetic operation circuit 61 is exemplified to perform the processing of retrieving data from the memory 63, the processing of setting the detection period, and the processing of calculating the propagation path length singly. However, these three types of processing may be performed by separate processing circuits.

In the present embodiment, the medium sensor 70 is exemplified to have both of the temperature sensor 71 and the composition sensor 72. However, the medium sensor 70 may have at least one of the temperature sensor 71 and the composition sensor 72. For example, in case that the medium sensor 70 does not include the composition sensor 72 but includes only the temperature sensor 71, the medium for transmitting the ultrasonic wave is determined in advance to gasoline, air or the like. In case that the medium sensor 70 does not include the temperature sensor 71 but includes only the composition sensor 72, the temperature of the medium for transmitting the ultrasonic wave is set to a fixed value in advance.

What is claimed is:

1. An ultrasonic distance measuring device for measuring a distance of an ultrasonic wave propagation path to a liquid surface of a liquid stored in a tank, the ultrasonic distance measuring device comprising:
    an ultrasonic element for generating an ultrasonic wave and converting an input ultrasonic wave into an electric signal;
    a transmitter circuit for outputting a drive signal to the ultrasonic element for generation of the ultrasonic wave;
    a comparator circuit for outputting a detection signal when the electric signal of the ultrasonic element exceeds a threshold level;
    a medium sensor for detecting a physical quantity of a medium of the propagation path; and
    a control circuit including a memory and an arithmetic operation circuit,
    wherein:
    the memory stores a correlation between the physical quantity and a propagation speed of the ultrasonic wave depending on the physical quantity, a longest propagation path length and a shortest propagation path length of the propagation path, and a length of a waveform of the electric signal;

the length of the waveform of the electric signal is a length of a range in which the electric signal obtained by converting the ultrasonic wave reflected by the liquid surface and input to the ultrasonic element is larger than a reference value;

the reference value is a predetermined value smaller than the threshold level used in the comparator; and the arithmetic operation circuit is programmed to execute processing of retrieving the propagation speed of the ultrasonic wave corresponding to an output of the medium sensor from the correlation between the physical quantity and the propagation speed of the ultrasonic wave, setting a propagation path detection period for detecting a liquid surface timing, at which the detection signal corresponding to the ultrasonic wave reflected by the liquid surface is output from the comparator circuit, based on the longest propagation path length and the shortest propagation path length, which are stored in the memory, and the propagation speed of the ultrasonic wave retrieved from the memory, calculating a difference of the propagation path based on a time difference between the liquid surface timing in the propagation path detection period and an output timing of outputting the ultrasonic wave from the ultrasonic element, and the propagation speed of the ultrasonic wave retrieved from the memory, storing, to the memory, the time difference between a calculated liquid surface timing and the output timing, setting the propagation path detection period based on the longest propagation path length and the shortest propagation path length stored in the memory and the propagation speed of the ultrasonic wave retrieved from the memory, in case the time difference between the liquid surface timing and the output timing is not stored in the memory, setting the propagation path detection period based on the time difference between the liquid surface timing and the output timing stored in the memory and the length of the waveform of the electric signal stored in the memory, in case the time difference between the liquid surface timing and the output timing is stored in the memory, and setting a width of the propagation path detection period to a value determined by multiplying the length of the waveform the electric signal by a coefficient which is equal to or larger than 1.

2. The ultrasonic distance measuring device according to claim 1, wherein: the memory further stores a correlation between the propagation speed of the ultrasonic wave and the length of the waveform of the ultrasonic wave; and the arithmetic operation circuit is further programmed to execute processing of setting the propagation path detection period based on the time difference between the liquid surface timing and the output timing stored in the memory and the length of the waveform of the ultrasonic wave corresponding to the propagation speed of the ultrasonic wave, in case the time difference between the liquid surface timing and the output timing is not stored in the memory.

3. The ultrasonic distance measuring device according to claim 2, wherein:
the arithmetic operation circuit is further programmed to execute processing of selecting, as the liquid surface timing, an output timing of a detection signal, which has a shortest time difference relative to the output timing, among plural detection signals output from the comparator circuit, in case the plural detection signals are output during the propagation path detection period.

4. The ultrasonic distance measuring device according to claim 2, wherein:
the liquid to be detected is fuel.

5. The ultrasonic distance measuring device according to claim 2, wherein:
the ultrasonic sensor is provided within the liquid stored in the tank.

6. The ultrasonic distance measuring device according to claim 2, wherein:
the medium sensor includes at least one of a temperature sensor for detecting a temperature of the medium and a composition sensor for detecting a composition of the medium and detects at least one of the temperature and the composition of the medium.

7. The ultrasonic distance measuring device according to claim 1, wherein:
the arithmetic operation circuit is further programmed to execute processing of selecting, as the liquid surface timing, an output timing of a detection signal, which has a shortest time difference relative to the output timing, among plural detection signals output from the comparator circuit, in case the plural detection signals are output during the propagation path detection period.

8. The ultrasonic distance measuring device according to claim 7, wherein:
the liquid to be detected is fuel.

9. The ultrasonic distance measuring device according to claim 7, wherein:
the ultrasonic sensor is provided within the liquid stored in the tank.

10. The ultrasonic distance measuring device according to claim 7, wherein:
the medium sensor includes at least one of a temperature sensor for detecting a temperature of the medium and a composition sensor for detecting a composition of the medium and detects at least one of the temperature and the composition of the medium.

11. The ultrasonic distance measuring device according to claim 1, wherein:
the liquid to be detected is fuel.

12. The ultrasonic distance measuring device according to claim 11, wherein:
the ultrasonic sensor is provided within the liquid stored in the tank.

13. The ultrasonic distance measuring device according to claim 11, wherein:
the medium sensor includes at least one of a temperature sensor for detecting a temperature of the medium and a composition sensor for detecting a composition of the medium and detects at least one of the temperature and the composition of the medium.

14. The ultrasonic distance measuring device according to claim 1, wherein:
the ultrasonic sensor is provided within the liquid stored in the tank.

15. The ultrasonic distance measuring device according to claim 1, wherein:
the medium sensor includes at least one of a temperature sensor for detecting a temperature of the medium and a composition sensor for detecting a composition of the medium and detects at least one of the temperature and the composition of the medium.

16. The ultrasonic distance measuring device according to claim 1, wherein:
the arithmetic operation circuit is further programmed to execute processing of;
setting the lower limit value of the propagation path detection period to tp−Lw/2, and
setting an upper limit value of the propagation path detection period to tp+Lw/2, where tp is a time difference between the liquid surface timing and the output timing, and Lw is the length of the waveform of the ultrasonic wave.

17. The ultrasonic distance measuring device according to claim 1, wherein:
the memory stores a correlation between the propagation speed and the length of the waveform of the electric signal.

18. The ultrasonic distance measuring device according to claim 1, wherein:
the memory stores the length of the waveform of the electric signal as a fixed value.

* * * * *